United States Patent [19]

Klocke et al.

[11] Patent Number: 5,047,242

[45] Date of Patent: Sep. 10, 1991

[54] AZADIRACHTIN DERIVATIVE INSECTICIDES

[75] Inventors: James A. Klocke, Salt Lake City, Utah; S. Mark Lee, Elkgrove, Calif.; Ronald B. Yamasaki, Salt Lake City, Utah

[73] Assignee: Native Plant Institute ("NPI"), Salt Lake City, Utah

[21] Appl. No.: 72,892

[22] Filed: Oct. 13, 1987

Related U.S. Application Data

[63] Continuation-in-part of Ser. No. 21,807, Mar. 4, 1987.

[51] Int. Cl.[5] .................. A01N 65/00; A01N 43/16; A01N 25/00; A61K 35/78
[52] U.S. Cl. .................. 424/195.1; 514/453; 514/65
[58] Field of Search .................. 424/195.1; 514/453, 514/65

[56] References Cited

U.S. PATENT DOCUMENTS

| | | | |
|---|---|---|---|
| 3,944,664 | 3/1976 | Kitagaki et al. | 514/25 |
| 4,287,186 | 9/1981 | Zähner et al. | 514/43 |
| 4,515,785 | 5/1985 | Shimizu et al. | 424/195.1 |
| 4,537,774 | 8/1985 | Shimizu et al. | 424/195.1 |
| 4,556,562 | 12/1985 | Larson | 424/195.1 |
| 4,666,747 | 5/1987 | Quinn | 514/65 |
| 4,822,614 | 4/1989 | Rodero | 514/718 |

OTHER PUBLICATIONS

Kubo et al., "Insect Ecdysis Inhibitors", in Natural Resistance of Plants to Pests, pp. 206–219, ACS Symposium Series 296 (1986).
Morgan, "Strategy in the Isolation of Insect Control Substances from Plants", Proc. 1st Int. Neem Conf., pp. 43–52 (Rottach-Egerm 1980), (Shmutterrer et al., Eds. 1982).
Butterworth et al., J. Chem. Soc. (Chem. Commun), pp. 23–24, (1968).
Qadri et al., Indian J. Exp. Biol. 16: 1141–1143 (1978).
Sieber et al., J. Insect Physiol. 29: 523–527 (1983).
Kubo et al., Agric. Biol. Chem. 46(7): 1951–1953 (1982).
Litchfield et al., J. Pharm. & Exp. Therapeutics 96: 99–113 (1949).
Yamasaki et al., J. Chromatog. 356: 220–226 (1986).
Truman et al., Nature 291: 70–71 (1981).
Truman, Amer. Zool. 21: 665–661 (1981).
Taylor et al., Abstract No. 177, Intnl. Res. Cong. on Nat. Pord, Chapel Hill, N.C. (Jul. 1985).
Broughton et al., J. Chem. Soc. (Chem. Commun.) 47, (1986).
Bokel et al., J. Chem. Soc. (Chem. Commun.) 523 (1986).
Kubo et al., "Plant Resistance to Insects", pp. 329–346, ACS Symposium Series 208, (1983).
Lee et al., J. Liq. Chromatog. 10(6): 1151–1163 (1987).

*Primary Examiner*—Ronald W. Griffin
*Attorney, Agent, or Firm*—Lyon & Lyon

[57] ABSTRACT

Derivatives of azadirachtin are described which should facilitate their synthesis and provide greater stability than their naturally-occurring counterpart. The derivative 2',3',22,23-tetrahydorazadirachtin is also described, that derivative retaining full activity and having enhanced stability. Also described is a newly identified, naturally occurring derivative of azadirachtin, 1-cinnamoylmelianolone, and several of its derivatives. Insecticidal and antifeedant compositions including these compounds, and processes for their use, are also described.

26 Claims, 2 Drawing Sheets

AZADIRACHTIN DERIVATIVE INSECTICIDES

RELATED APPLICATIONS

This is a continuation-in-part of Application Ser. No. 021,807, filed Mar. 4, 1987.

FIELD OF THE INVENTION

The field of the invention is insecticides. More specifically, it relates to insecticidal and antifeedant derivatives of naturally occurring insect ecdysis inhibitors.

BACKGROUND OF THE INVENTION

A requisite for developmental growth in insects is molting. Molting is the entire process by which an insect's old cuticle is shed. The process of molting is initiated when the insect molting hormone ecdysterone (20-hydroxyecdysone) stimulates the epidermis to retract from the cuticle. This retraction of the epidermis from the cuticle is termed "apolysis". Apolysis is immediately followed by mitotic division of the epidermal cells and their subsequent secretion of a protective procuticle and a gel-like molting fluid.

Following activation of the molting fluid, enzymatic digestion of the old cuticle for resorption and reuse results in a thin (i.e., undigested) remnant of the old cuticle which is subsequently split and cast off by the insect. This remnant of the old cuticle which is eventually split and cast off is called the "exuvia". The casting off of the exuvia is termed "ecdysis". Ecdysis is accomplished by hydrostatic pressure brought about by the swallowing of air or water by the insect and its subsequent performance of muscular activities.

When a new cuticle is synthesized, it is soft and flexible so that the hydrostatic pressures brought about by the insect unfold and expand it. In this way, the new cuticle increases its surface area and the old cuticle is concomitantly cast off.

After ecdysis, expansion of the new cuticle is brought to an end by the onset of "sclerotization". Sclerotization involves the cross-linking of cuticular protein with orthoquinone. The source of the ortho-quinone is tyrosine, whose mobilization is controlled by ecdysterone and a peptide hormone called bursicon.

Thus, the major events of the molting process are apolysis (retraction of the cuticle), cuticular synthesis, ecdysis (casting off of the exuvia), and sclerotization. The complexity of the sequence of the physiological and developmental events occurring in the molting process, and the high degree of hormonal coordination with which the entire process must proceed render the insect particularly vulnerable to exogenously applied chemicals.

The present invention deals with naturally-occurring chemicals and derivatives thereof which inhibit or prevents ecdysis.

As noted, the actual shedding of the cuticle is termed ecdysis. Ecdysis is triggered by a neurosecretory peptide called "eclosion hormone" which acts on the central nervous system to elicit the ecdysial motor programmes. Truman, J. W., et al., *Nature (London)* 291:70-1 (1981). The release of eclosion hormone is in turn regulated by the molting hormone ecdysterone. Truman, J. W., *Amer. Zool.* 21:655-61 (1981). The inhibition of ecdysis, which can occur through a disruption of the normal titres of ecdysterone or eclosion hormone, is easily observed as a gross morphological event in which the "old" cuticle remains enveloping the insect in the pharate condition. The abnormal pharate condition prevents the feeding and locomotion of the affected insect and eventually results in death. A number of ecdysis inhibitors, including ecdysterone, JH (Juvenile Hormone), and phenylurea compounds are known and have previously been discussed. Kubo & Klocke, "Insect Ecdysis Inhibitors," in "Natural Resistance of Plants to Pests (Roles of Allelochemicals)", ACS Symposium Series 296 (Green and Hedin eds.) Chapter 17, pages 206-219 (American Chemical Society 1986). This and all other publications referred to herein are incorporated by reference.

A natural plant compound which is known to inhibit ecdysis in insects, by some unknown mechanism, is azadirachtin. Morgan, "Strategy in the Isolation of Insect Control Substances From Plants," Proc. First Inter. Neem Conf. pages 43-52 (Rottach-Egern 1980). Azadirachtin is a tetranortriterpenoid of the limonoid type isolated from the seeds of the neem tree (*Azadirachta indica*) and has been reported to have been isolated from the fruits of the chinaberry tree (*Melia azedarach*). Butterworth, J. H., et al., J. Chem. Soc., Chem. Commun. 23-4 (1968). The skeletal structure and stereochemistry of azadirachtin have now been resolved. Broughton et al., *J. Chem. Soc.* (Chem. Commun.) 47 (1986); Bokel et al., *J. Chem. Soc.* (Chem. Commun.) 523 (1986). The potent ecdysis inhibitory activity of this compound is well-known. Qadri, S. S. H., et al., *Indian J. Exp. Biol.* 16:1141-3 (1978); Sieber, K. P., et al., *J. Insect Physiol.* 29:523-7 (1983); Kubo, I., et al., *Agric. Biol. Chem.* 46:1951-53 (1982).

Another natural product which was isolated from the neem tree and found to have ecdysis inhibitory activity is deacetylazadirachtinol. Although deacetylazadirachtinol was shown in one study to be about 2.5-fold less active than azadirachtin as an insect growth inhibitor, in that same study the two compounds were shown to have the same ecdysis inhibitory activity (Kubo & Klocke, supra).

SUMMARY OF THE INVENTION

Derivatives of azadirachtin are described which should facilitate their synthesis and provide greater stability than their naturally-occurring counterpart. The derivative 2',3',22,23-tetrahydroazadirachtin is also described, that derivative retaining full activity and having enhanced stability. Insecticidal and antifeedant compositions including these compounds are also described.

Also described is a new tetranortriterpenoid isolated and purified from the chinaberry tree, 1-cinnamoylmelianolone, and several derivatives, including 1-cinnamoyl-3-O-acetylmelianolone, and 1-cinnamoyl-3,19-O,O-diacetylmelianolone.

DETAILED DESCRIPTION OF THE INVENTION

Several derivatives of azadirachtin were prepared and their structures confirmed by infrared and nuclear magnetic resonance spectroscopy.

Referring to the numbered compounds of Table 1, transesterification of azadirachtin (1) with sodium methoxide gave 3-deacetylazadirachtin (2). Heating a solution of azadirachtin (1) and acetic anhydride at reflux gave a monoacetylated product, 11-O-acetylazadirachtin (4).

Treatment of azadirachtin (1) with iodomethane and silver (I) oxide gave monomethylated product, most likely 11-O-methylazadirachtin (5), as shown by IR and $^1$H-NMR spectroscopy.

22,23-dihydroazadirachtin (3) was made by hydrogenation of azadirachtin over platinum (IV) oxide at 5 atm pressure. 2',3',22,23-tetrahydroazadirachtin (8) was made by hydrogenation of azadirachtin over palladium catalyst, which was successful only when using elevated pressures.

The tigloyl group was removed by oxidizing 22,23-dihydroazadirachtin (3) with osmium tetroxide and excess sodium periodate and then hydrolyzing the resulting pyruvate ester with mild aqueous alkali. The product was 1-detigloyl-22,23-dihydroazadirachtin (7). When this reaction sequence was repeated using an amount of sodium periodate approximately equimolar with 22,23-dihydroazadirachtin (3), 2',3'-dihydroxy-2',3',22,23-tetrahydroazadirachtin (9) was obtained in about 50% yield.

Heating 22,23-dihydroazadirachtin (3) with dimethyl pyrocarbonate gave a dicarbomethoxylated product, unlike the acetylation reaction where only one hydroxyl group esterified. The structure most consistent with IR and NMR spectra is 11,20-O, O-dicarbomethoxy-22,23-dihydroazadirachtin (6).

The results of the growth inhibitory and lethal activities of azadirachtin and these 8 derivatives when fed in an artificial diet to *Heliothis virescens* larvae are shown in Table 1. Similar to the results of Morgan, E. D., in "Natural pesticides from the Neem tree (*Azadirachta indica* A. Juss), Schmutterer, H., et al., Eds., Proc. First International Neem Conference (Rottach-Egern, 1980), German Agency for Technical Corporation, Eschborn, Germany, 1982, pps. 43–52 (hereinafter "Morgan"), neither deacetylation nor hydrogenation of the carbon-carbon double bond of the dihydrofuran ring moiety of azadirachtin had any significant effect on activity of the compound against *H. virescens*.

Also similar to the structure-activity results of Morgan was the finding that acetylation of the hydroxyl group at position 11 resulted in a slight decrease in the activity of the natural rroduct. More effective in the reduction of activity at this position was methylation. Other derivatives made at the hydroxyl groups at positions 11 and 20 also resulted in diminished activity. For example, derivatization of these hydroxyl groups with trimethylsilyl groups (Morgan) or with dimethylpyrocarbonate to yield the dicarbomethoxy derivatives resulted in decreased activity.

The Table 1 data indicate that the tetrahydro derivative of azadirachtin, 2',3',22,23-tetrahydroazadirachtin, is fully active. Other results described below further demonstrate that this derivative is more stable than the natural product.

TABLE 1

Mortality and growth inhibition in first-instar *Heliothis virescens* larvae fed azadirachtin and eight derivatives in an artificial diet (I. Kubo and J. A. Klocke, In: Plant Resistance to Insects (P. A. Helin, Ed.), ACS Symposium Series 208, American Chemical Society, Washington, D.C. (1983), pp. 329–346.).[a]

| | Test Compound | LC$_{50}$ (ppm)[b] | EC$_{50}$ (ppm)[c] |
|---|---|---|---|
| 1. | azadirachtin | 0.80 (0.46–1.39) | 0.07 (0.05–0.10) |
| 2. | 3-deacetylazadirachtin | 0.37 (0.17–0.80) | 0.09 (0.05–0.17) |
| 3. | 22,23-dihydroazadirachtin | 0.47 (0.32–0.67) | 0.08 (0.04–0.15) |
| 4. | 11-O-acetylazadirachtin | 0.95 (0.59–1.54) | 0.18 (0.08–0.40) |
| 5. | 11-O-methylazadirachtin | 25.0 (12.2–51.4) | 5.00 (1.54–16.25) |
| 6. | 11,20-O,O-dicarbomethoxy-22,23-dihydroazadirachtin | 90.0 (37.8–214.5) | 29.0 (20.3–41.5) |
| 7. | 1-detigloyl-22,23-dihydroazadirachtin | 2.40 (1.15–5.02) | 0.59 (0.30–1.14) |
| 8. | 2',3',22,23-tetrahydroazadirachtin | 0.30 (0.11–0.80) | 0.08 (0.05–0.13) |
| 9. | 2',3'-dihydroxy-2',3',22,23-tetrahydroazadirachtin | 42.0 (32.3–54.6) | 3.80 (1.95–7.41) |

[a]Similar results were obtained against the corn earworm (*Heliothis zea*) and the fall armyworm (*Spodoptera frugiperda*).
[b]LC$_{50}$ values are the concentrations (ppm) causing 50% mortality.
[c]EC$_{50}$ values are the concentrations (ppm) causing 50% growth inhibition.
[d]Numbers in parentheses are the 95% confidence limits determined using the methods of Litchfield and Wilcoxon, J. Pharmacol. Exp. Ther. 96:99–113 (1949).

EXPERIMENTAL NO. 1

Solvents used for high performance liquid chromatography (HPLC) were of HPLC grade. Other chemicals were of reagent grade or better and were used without further purification unless noted otherwise.

Preparative HPLC was carried out with a Micromeritics Model 750 Solvent Delivery System equipped with a Negretti and Zambra injector, a Micromeritics Model 787 variable wavelength UV/VIS detector, a Hewlett-Packard 3388A integrator/recorder and a Gilson Model 201 fraction collector. Chromatography was accomplished using either a normal phase Alltech Associates silica gel (10µm particle size) stainless steel column (25×1.0 cm I.D.) protected with an Alltech Associates stainless steel guard column (5.0×0.46 cm I.D.) packed with Alltech Associates pellicular silica gel or a reversed phase Regis Chemical Company octadecylsilyl-silica gel (ODS) (10µm particle size) stainless steel column (25×1.0 cm I.D.), protected with an Alltech Associates stainless steel guard column (5.0 ×0.46 cm I.D.) packed with Alltech Associates pellicular ODS. The solvent (vide infra) was eluted at a flow rate of 5.00 ml/min.

Analytical HPLC was performed as described by Yamasaki et al, 1986. All prepared derivatives of azadirachtin were purified to greater than 98% purity. Azadirachtin was isolated and purified from neem seeds by the method of Yamasaki, R.B., et al. *J. Chromatogr.* 356:220–226 (1986) (hereinafter "Yamasaki et al.").

Azadirachtin (30mg, 0.042mmol) and 0.5ml of ethanol was stirred with 20mg of 5% palladiumon alumina at 20° C. under hydrogen (10 atm) for 3 hours. The reaction mixture was then filtered and rotary evaporated in vacuo. The crude product was purified by silica gel preparative HPLC (solvent=2-propanol:n-hexane, 17:83, v/v), followed by ODS preparative HPLC (solvent=methanol:water, 1:1, v/v) to give 2',3',22,23-tetrahydroazadirachtin (18mg).

Stability of Azadirachtin derivatives was determined as follows:

Azadirachtin, 3-deacetylazadirachtin, 22,23-dihydroazadirachtin, and 2',3',22,23-tetrahydroazadirachtin (1.0 mg/ml absolute ethanol) were placed individually in capped quartz NMR tubes (5×180 mm) and were irradiated with two UV germicidal lights (GE, G30T8, 200–280 nm, 30W) 1.8 m from the source at room temperature for up to 400 h. The controls were identical samples protected from exposure to UV radiation by wrapping with aluminum foil. At selected time intervals, aliquots from both the controls (non-irradiated) and irradiated samples were removed for high-performance liquid chromatography (HPLC) analysis and bioassay (vide infra).

Analytical reversed phase HPLC was performed on a phenyl (5μm) column run isocratically with acetonitrile-water (3:7) (Yamasaki et al.) Peaks were detected at 214 nm. The irradiated samples were compared with their corresponding non-UV-irradiated controls by measuring the height of the peak eluting at the appropriate $R_t$ for each irradiated compound relative to each one's non-irradiated control. Results are expressed as the percent of the initial sample concentration remaining relative to the control. Each time point was done in at least triplicate fashion.

Individual larvae were injected per os on the first day of the fifth instar with 1.0 μg of either irradiated or non-irradiated compounds dissolved in 1.0 μl of 75% aqueous ethanol. The activity of the non-irradiated compounds is shown in Table 2. Azadirachtin and 2',3',22,23-tetrahydroazadirachtin were equally effective in inhibiting pupation of *H. virescens* larvae (i.e., in reducing the number of larvae that developed into pupae). 3-deacetylazadirachtin and 22,23-dihydroazadirachtin were less effective. However, all four compounds strongly inhibited the development of the larvae to the adult stage. The ability of these compounds to inhibit pupation and the emergence of morphologically normal adults was expressed as the ratio between the percentage of larvae that failed to pupate (Table 3) or to reach the adult stage (Table 4) when injected with irradiated and when injected with the corresponding non-irradiated compounds, multiplied by 100%.

The activity of the irradiated compounds, relative to the activity of the non-irradiated compounds, is shown in Tables 3 and 4. The ability of azadirachtin, 3-deacetylazadirachtin, and 22,23-dihydroazadirachtin to inhibit pupation was not appreciably reduced by up to 90 h of exposure to the UV radiation, but did decline, for all three compounds, after 200 h of exposure. An even greater decline in the ability of these three compounds to inhibit pupation was noted after 400 h of exposure. 2',3',22,23-tetrahydroazadirachtin was most active in inhibiting pupation after 200 h of UV exposure, and although its activity declined after 400 h of exposure, it was still more active than the other test compounds (Table 3).

Similar to the results in Table 3, 90 h of exposure to the UV radiation did not reduce the ability of the four compounds to inhibit the larvae from reaching the adult stage (Table 4). After 200 h of irradiation, the activity of azadirachtin declined sligtly and that of 22,23-dihydroazadirachtin more so. The activity of 3-deacetylazadirachtin remained substantially unchanged until 400 h of irradiation. 2',3',22,23-tetrahydroazadirachtin, however, was fully active after 400 h of irradiation.

Using reversed phase HPLC, the relative retention times ($R_t$) were determined, at 214 nm, to be 10.2, 7.5, 9.0, and 9.9 min, for azadirachtin, 3-deacetylazadirachtin, 22,23-dihydroazadirachtin, and 2',3',22,23-tetrahydroazadirachtin, respectively. Thus, azadirachtin, 3-deacetylazadirachtin, and 22,23-dihydroazadirachtin were found to be UV-labile (FIG. 1) and, under the conditions used, the three compounds appeared to be degraded in a first-order reaction (data not shown). Furthermore, all three compounds degraded at essentially the same rate ($T_{½}$=25 h). In sharp contrast, 2',3',22,23-tetrahydroazadirachtin exhibited no degradation following 200 h of exposure to UV radiation, and only slight degradation following 400 h of exposure (FIG. 1). HPLC analysis of the non-irradiated compounds showed no change throughout the experiment in the heights of the peaks eluting at the appropriate $R_t$'s.

TABLE 2

| | Number Larvae | Unsuccessful Larvae-Pupae | Number Pupae | Unsuccessful Pupae-Adult | Number Adults | Number Adults Deformed | % Mortality Prior to Adult Stage |
|---|---|---|---|---|---|---|---|
| Azadirachtin | 149 | 5 | 10 | 0 | 2 | 1 | 98.7 |
| % | 3.4 | 6.7 | 0 | 1.3 | 0.7 | | |
| 3-Deacetyl-azadirachtin | 169 | 13 | 56 | 4 | 10 | 10 | 94.1 |
| % | 7.7 | 33.1 | 2.4 | 5.9 | 5.9 | | |
| 22,23-Dihydro-azadirachtin | 176 | 13. | 47 | 4 | 6 | 5 | 96.6 |
| % | 7.4 | 26.7 | 2.3 | 3.4 | 2.8 | | |
| 2',3',22,23-Tetrahydro azadirachtin | 135 | 6 | 10 | 1 | 0 | 0 | 100 |
| % | 4.4 | 7.4 | 0.7 | 0 | 0 | | |

Table 2: Successful and unsuccessful pupal and adult development of fifth-instar *Heliothis Virescens* larvae injected orally with 1.0 microgram of either azadirachtin, 3-deacetylazadirachtin, 22,23-dihydroazadirachtin, or 2',3',22,23-tetrahydroazadirachtin.

TABLE 3

|       | Azadirachtin | 3-Deacetyl-azadirachtin | 22,23-Dihydro-azadirachtin | 2',3',22,23-Tetra hydroazadirachtin |
|-------|--------------|-------------------------|----------------------------|-------------------------------------|
| 15 h  | 98.6         | 115.2                   | 113.1                      | 99.4                                |
| 30 h  | 98.9         | 135.0                   | 104.6                      | 103.7                               |
| 90 h  | 85.7         | 139.5                   | 100.0                      | 99.7                                |
| 200 h | 74.2         | 86.8                    | 72.7                       | 108.0                               |
| 400 h | 60.0         | 41.0                    | 49.1                       | 69.1                                |
| N =   | 127          | 152                     | 150                        | 128                                 |

Table 3: Relative activity of azadirachtin, 3-deacetylaza-dirachtin, 22,23-dihydroazadirachtin, and 2',3',22,23-tetrahydroazadirachtin, all of which had been exposed for 15, 30, 90, 200, and 400 hours to UV radiation, inhibiting the pupal development of fifth-instar *Heliothis virescens* larvae. Relative activity is defined as the percentage of larvae injected with each irradiated compound that failed to pupate relative to the percentage injected with its non-irradiated counterpart that failed to pupate, times 100.

TABLE 4

|       | Azadirachtin | 3-Deacetyl-azadirachtin | 22,23-Dihydro-azadirachtin | 2',3',22,23-Tetra hydroazadirachtin |
|-------|--------------|-------------------------|----------------------------|-------------------------------------|
| 15 h  | 101.3        | 103.2                   | 103.5                      | 100.0                               |
| 30 h  | 101.3        | 106.3                   | 100.1                      | 100.0                               |
| 90 h  | 97.3         | 106.3                   | 103.5                      | 100.0                               |
| 200 h | 89.7         | 96.0                    | 69.0                       | 100.0                               |
| 400 h | 81.1         | 72.3                    | 74.5                       | 100.0                               |
| N =   | 127          | 152                     | 150                        | 128                                 |

Table 4: Relative activity of azadirachtin, 3-deacetylaza-dirachtin, 22,23-dihydroazadirachtin, 2',3',22,23-tetrahydroaza-dirachtin, all of which had been exposed for 15, 30, 90, 200, and 400 hours to UV radiation, in inhibiting the adult development of fifth-instar *Heliothis virescens* larvae. Relative activity is defined as the percentage of larvae injected with each irradiated compound that failed to reach the adult stage relative to the percentage injected with its non-irradiated counterpart that failed to reach the adult stage, times 100.

That azadirachtin, 3-deacetylazadirachtin, and 22,23-dihydroazadirachtin were UV-labile as indicated using HPLC, may best be explained by the presence in each compound of a tigloyl group. This alpha, beta-unsaturated carbonyl moiety is a strong chromophore and perhaps the major site of chemical degradation since the three compounds that contain it show the same rate of reaction. 2',3',22,23-tetrahydroazadirachtin does not contain a strong chromophore, i.e., the tigloyl group is reduced to a saturated cabonyl system, and it is, hence, not UV-labile.

Apparently, one or more of the UV-degradation products of azadirachtin, 3-deacetylazadirachtin, and 22,23-dihydroazadirachtin were as active as the native molecules. For instance, more than 80% of the three compounds was degraded after 90 h of exposure to UV radiation, yet all three retained full activity. After 400 h of exposure, none of the three compounds remained in their original state, yet all three retained approximately 50% of their activity. In the case of 2',3',22,23-tetrahydroazadirachtin, only after 400 h of exposure to UV radiation was any degradation noted, and this degradation led to some loss in activity. Thus, while 2',3',22,23-tetrahydroazadirachtin was definitely more stable than were the other three compounds to UV-degradation, decreased chemical stability did not translate into decreased biological activity until 200 h of exposure to UV radiation. The chemical nature of the fully active degradation products of azadirachtin, 3-deacetylazadirachtin, and 22,23-tetrahydroazadirachtin, formed through exposure to UV radiation for up to 90 h, is unknown.

EXPERIMENTAL NO. 2

Referring to the numbered compounds of Table 5, we have also discovered and purified a new insecticidal tetranortriterpenoid, 1-cinnamoylmelianolone (10), which was isolated from methanolic extracts of the fruit of the chinaberry or Persian lilac (*Melia azedarach* L.). We also isolated derivatives of that compound including, 1-cinnamoyl-11-hydroxymeliacarpin (11). Insecticidal activities of these compounds were compared using 2 lepidopterous species, *Heliothis virescens* and *Spodoptera frugiperda*.

Green chinaberry fruits were collected and stored at 4° C. until extraction, which was accomplished as follows.

Extraction. Fresh fruits (5.7 kg weight) were homogenized in methanol (ca 0.5 g/ml) for 5 min with a Waring blender. The methanolic homogenate was allowed to stand at room temperature for 24 hours with occasional stirring before filtering through several layers of cheesecloth followed by Whatman #3 filter paper. The remaining marc was reextracted twice more in the same manner described above. The methanolic extracts were pooled and concentrated on the rotary evaporator at 40° C. at which point a green pigment precipitated. The concentrated extract was stored at 4° C. to enhance further precipitation of pigments and lipids. After 24 hour storage at 4° C., the precipitate was filtered off and the filtrate was partitioned with hexane (3×) and methylene chloride (3×). Greenish orange methylene chloride partition fractions were pooled and concentrated on a rotary evaporator at 40° C. to dryness (6.6 g).

Flash Column Chromatography. A 2.0 liter flash column (Aldrich) was packed, after removal of fines, with silica gel (500 g, 240-400 mesh, J. T. Baker) and equilibrated with a mixture of n-hexane and ethyl acetate (3:2). The residue (6.6 g) from the methylene chloride partition described above was dissolved in 100 ml of methylene chloride and applied onto the top of the column. The column was then eluted stepwise with the following solvent mixtures (n-hexane-ethyl acetate (3:2, 2 1); n-hexane-ethyl acetate-isopropanol (60:39:1, 1 1); n-hexane-ethyl acetate-isopropanol (54:39:10, 1 1); methanol (1 1). Effluents from the different solvent mixtures were collected separately and analyzed for compounds 10 and 11 with thin layer chromatography (TLC) (vide infra).

Low Pressure Column Chromatography. A low pressure column (Michael-Miller, 4 cm I.D.×35 cm, Ace Glass) was packed with octadeylsilyl-silica gel (500 g, 40 μm, Regis) and equilibrated with aqueous methanol (60% methanol). The above column chromatography fraction containing 10 and 11 (n-hexane-ethyl acetate-isopropanol, 54:39:10, 2.5 g) described above was dissolved in 5 ml methanol and loaded onto the column. The column was eluted with aqueous methanol (60% methanol) at 4 ml/min. and the column effluent was collected every 6 min. Fractions containing 10 and 11, monitored with TLC, were pooled and concentrated to dryness (1.38 g).

Droplet Counter-Current Chromatography (DCCC). Chromatography was carried out on an Eyela Model DCC-300-G3 Droplet Counter-Current Chromatography (Tokyo Rikakikai, Tokyo, Japan) equipped with 300 standard glass tubes (40×0.2 cm I.D.) interconnected with teflon tubing (0.5 mm I.D.). The DCCC solvent system, chloroform-toluene-methanol-water (5:5:8:2, v/v/v/v), was modified from S. M. Lee and J. A. Klocke, *J. Liq. Chromatogr.*, in press (1987). The top and bottom layers of the solvent mixture were used as the stationary and mobile phases, respectively. The low-pressure ODS column fraction (1.38 g) described above was dissolved in a 1:1 (v/v) mixture (10ml) of both mobile and stationary phases and loaded into the sample chamber. The flow rate was set at 4.0 ml/h and the effluent was collected in 4.0 ml fractions. Fractions containing 10 and 11 were pooled separately and concentrated in vacuo to yield 200 mg and 300 mg, respectively.

Thin Layer Chromatography (TLC). TLC was performed either on 40×8 mm Polygram SILG/UV254, (0.25 mm, Machere Nagel) or on 20×20 cm prescored silica gel GHLF (0.25 mm, Analtech) plates. The plates were developed with the bottom layer of the DCCC solvent mixture vide supra and visualized by spraying with a vanillin-sulfuric acid-ethanol (3 g:1 ml:100 ml) spray reagent followed by heating.

High Performance Liquid Chromatography (HPLC). Normal and reversed phase preparative and reversed phase analytical HPLC procedures used were slight modifications of the methods of Yamasaki et al. Effluents were detected using either a Micromeritics 787 variable-wavelength UV-Visible detector set at 218 nm or a Pharamcia single path monitor UV-1/214 with a 280 nm filter.

The normal phase preparative HPLC step was performed with a Phenomenex Maxsil 5 silica column (particle size 5μm, 25×2.0 cm I.D.) eluted isocratically with n-hexane-ethyl acetate-isopropanol (6:3:1, v/v/v) at a flow rate of 5.0 ml/min and an average pressure of 400 p.s.i. The reversed phase preparative HPLC step was performed with a Phenomenex Ultrex 5 phenyl column (particle size 5μm, 25×2.25 cm I.D.) eluted isocratically with acetonitrile-water (3:7, v/v) at a flow rate of 4 ml/min and an average pressure of 2100 p.s.i. Both columns were protected with an Alltech stainless-steel guard column (5.0×0.46 cm I.D.) packed with the corresponding Alltech pellicular packing material.

Reversed phase analytical HPLC was performed using the same phenyl column system as that described for azadirachtin (Yamasaki et al.). Analytical normal phase HPLC was performed on an Alltech silica gel column (5 μm, 25×0.46 cm I.D.) eluted isocratically with n-hexane-ethyl acetate-isopropanol (6:3:1) at a flow-rate of 1.0 ml/min and n average pressure of 500 p.s.i.

1-cinnamoylmelianolone exhibited the following spectral data: IR (KBr): 3700–3200, 2930, 1710, 1670, 1640 and 760 cm$^{-1}$; UV (CH$_3$OH): λ279 and 217 nm ( ε: 14500 and 7750); $^1$H-NMR: Table 6; C13-NMR: Table 7; FAB-MS: m/z 621 (M-H$_2$O+H)$^+$, 603 (M-2H$_2$O+H)$^+$, 585 (M-3H$_2$O+H)$^+$ and 131 (C$_9$H$_7$O)$^+$; FAB-MS salt (NaCl) dosing[6]) (glycerol:methanol (1:1) matrix): m/z 661 (M+Na)$^+$, corresponding to molecular weight 638 (molecular formula, C$_{35}$H$_{42}$O$_{11}$). $^{13}$C-NMR (DEPT spectra) and $^1$H-NMR (D$_2$O exchange) data indicate that the compound contains 4 CH$_3$, 4 CH$_2$, 18 CH, 9 carbonyls not bonded to hydrogen, and 4 protons due to OH groups. Furthermore, NMR spectral data suggest that the structure of 1-cinnamoylmelianolone is similar to that of azadirachtin except for the following.

Acetylation of 1-cinnamoylmelianolone with acetic anhydride in pyridine yielded a mixture of two products. The mixtures were separated and purified with HPLC as previously described. The products were 1-cinnamoyl-3-0-acetylmelianolone (12) and 1-cinnamoyl-3,19-0,0-diacetylmelianolone (13).

Reductive deesterification of 1-cinnamoylmelianolone yielded decinnamoylmelianolone (14) when NaBH$_4$ was added to 1-cinnamoylmelianolone (about 6 mg.) methanol (1ml) and incubated at 60° C. for one half hour. The workup was performed by diluting the reaction mixture with an equal volume of H$_2$O and extracting with diethyl ether. The diethyl ether extract was purified further with HPLC as described previously.

An artificial diet feeding bioassay with neonate larvae of tobacco budworm (*Heliothis virescens*) and fall armyworm (*Spodoptera frugiperda*) was used as previously described (Kubo and Klocke, 1983) to detect insecticidal activities in the plant extracts to monitor fractionation, and to determine the potency of the isolated constituents and derivatives. Potency was determined either as the effective concentration (EC50) of added material that is necessary to reduce larval growth to 50% of the control values or as the lethal concentration (LC50) of added material that is necessary to kill 50% of the treated larvae. EC50 and LC50 values were determined from log probit paper and analyzed statistically by the method of Litchfield and Wilcoxon, supra. The results are shown in Table 5 below.

Figure 1:
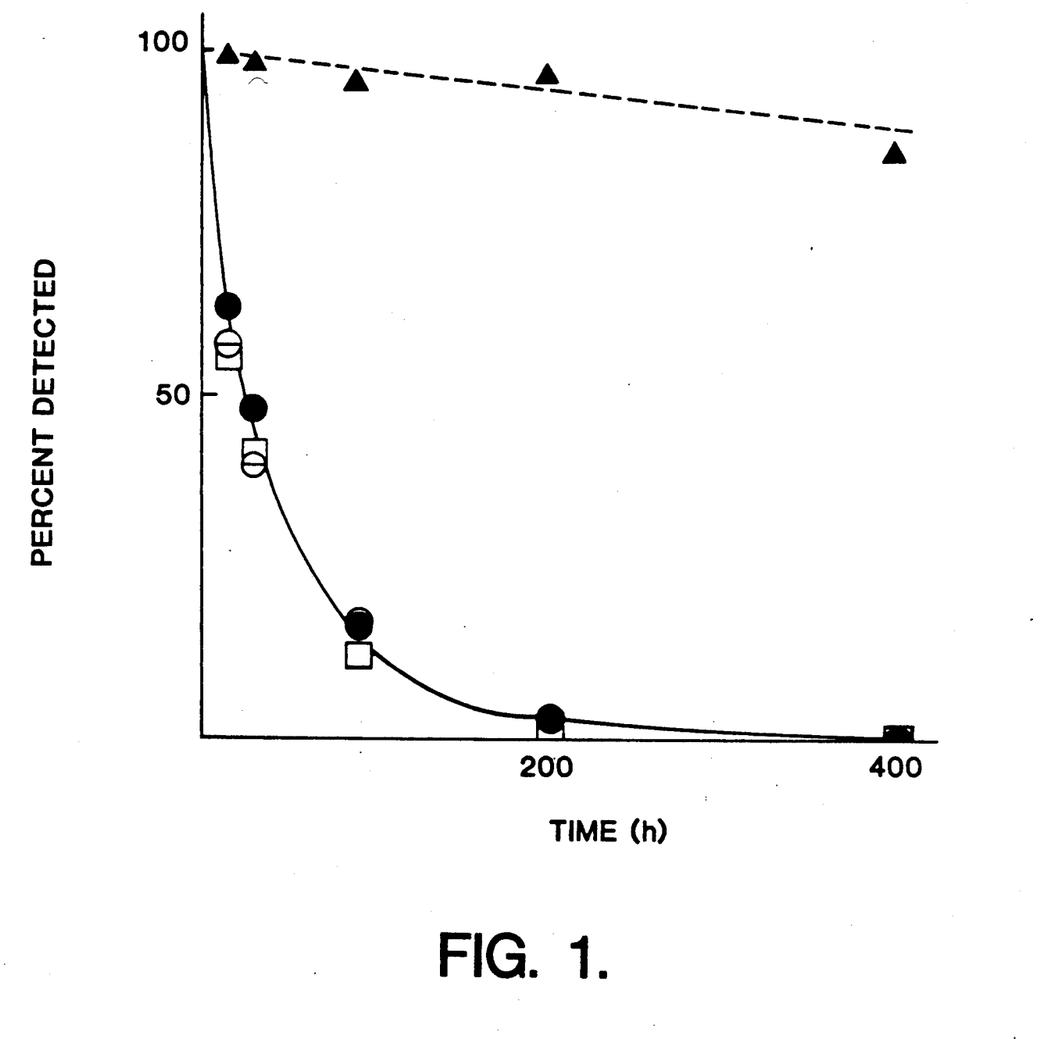
Figure 2A:
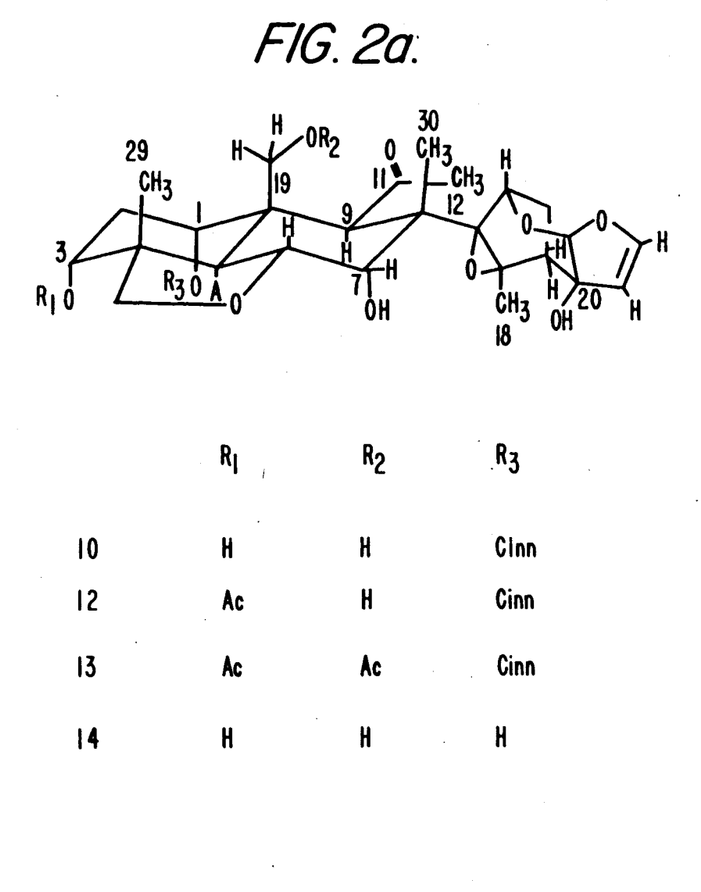
Figure 2B:
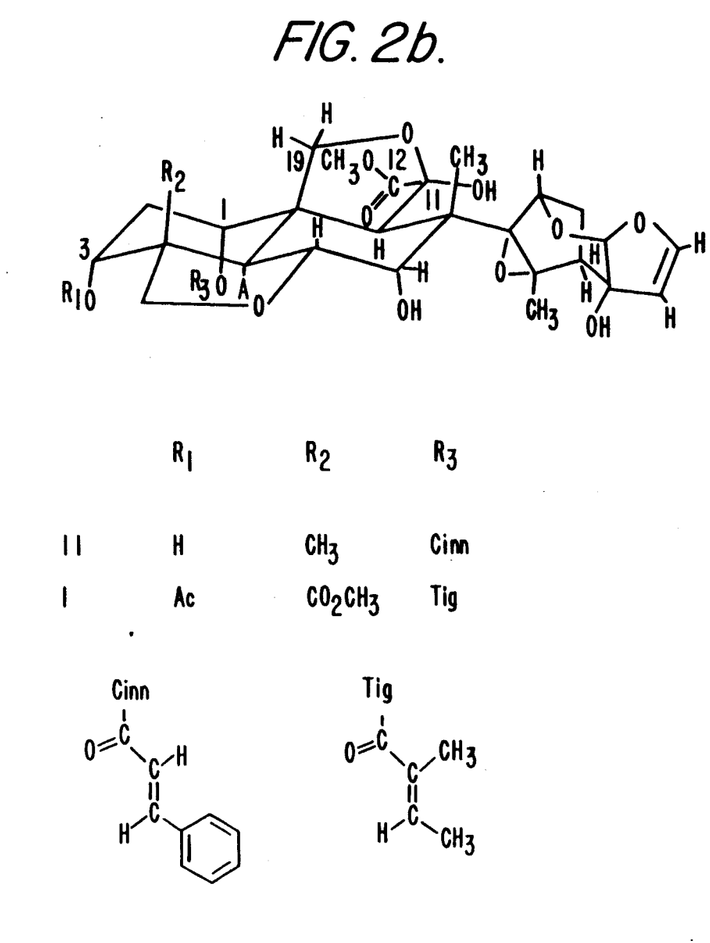

The proposed structures of azadirachtin and 1-cinnamoylmelianolone are shown in FIG. 2 as compounds 1 and 10, respectively. Test compound 12 is the monoacetate form of 1-cinnamoylmelianolone, having an acetyl group at R$_1$. Test compound 13 is the diacetate form of 1-cinnamoylmelianolone, having acetyl groups at R$_1$ and R$_2$. 1-cinnamoylmelianolone, test compound 12, and test compound 13, each have about the same insecticidal activity, which appears to be approximately half that of azadirachtin.

Test compound 14, decinnamoylmelianolone, did not show good activity. Presumably, this is because of the loss of the lipophilic cinnamate substituent. Similar loss of activity was seen upon removal of the lipophilic tiglate group from azadiractin (Table 1, test compound 7), and it is believed that a lipophilic substituent is needed at the R$_3$ position.

The claimed compositions have also been determined to function as antifeedants, as we have determined that isolated azadiractin does. To be effective as an antifeedant, a chemical should have a systemic mode of action.

In other words, the chemical, when applied to the plant or on or about its roots, must be taken up by the plant so that as it grows it is distributed to protect new tissue as well as old. This prevents having to more frequently respray growing crops or to reapply the compositions to reach the roots of those crops. The claimed compositions are systemic.

It is anticipated that, for example, tetrahydroazadirachtin in the amount of 50 grams per acre in an acceptable carrier would be sufficient to enable it to function as both an insecticide and as an antifeedant. It is believed that the concentration of tetrahydroazadirachtin, for example, utilized for either function should be at least about 5 grams per acre. Of course, the claimed compositions may also be utilized to protect stored crops from foraging insects, and a lesser amount of these antifeedant and insecticidal compositions may be useful to protect such crops that may be, for example, maintained in bins or graineries.

TABLE 5

Growth and larvicidal effects of 1-cinnamoylmelianolone and three derivatives fed in artifical diet to first instar larvae of *Heliothis virescens*.

| Test Compound | | EC50 (ppm) | LC50 (ppm) | 95% Confidence Limit |
|---|---|---|---|---|
| 10 | 1-Cinnamoylmelianolone | 0.12 | | 0.19–0.08 |
| | | | 1.50 | 2.34–0.96 |
| 12 | 1-Cinnamoyl-3-O,acetyl-melianolone | 0.15 | | 0.27–0.10 |
| | | | 1.50 | 2.74–0.82 |
| 13 | 1-Cinnamoyl-3,19-O,O-diacetylmelianolone | 0.12 | | 0.17–0.09 |
| | | | 1.50 | 3.33–0.68 |
| 14 | Decinnamoylymelianolone | 3.20 | | 8.11–1.26 |
| | | | 10.0 | — |

The above experiments are to assist in understanding the invention and should not, of course, be construed as specifically limiting the invention described and claimed herein. Such variations of the invention which would be within the purview of those in the art, including the substitution of all equivalents now known or later developed are to be considered to fall within the scope of the invention as hereinafter claimed.

We claim:

1. A substantially pure compound of the formula

-continued wherein $R_1$ is H or acetyl, $R_3$ is H or acetyl and $R_3$ is a lipophilic group.

2. A compound according to claim 1 wherein $R_3$ is a saturated or unsaturated fatty acid of at least $C_3$ length.

3. A compound according to claim 2 wherein $R_3$ is cinnamoyl or tigloyl.

4. A compound according to claim 3 wherein $R_3$ is cinnamoyl.

5. The compound according to claim 4 which comprises 1-cinnamoylmelianolone.

6. The compound according to claim 4 which comprises 1-cinnamoyl-3O-acetylmelianolone.

7. The compound according to claim 4 which comprises 1-cinnamoyl-3,19-O,O-diacetylmelianolone.

8. A composition comprising an insecticidally effective amount of the compound of claim 1 and an acceptable carrier.

9. A composition comprising an insecticidally effective amount of the compound of claim 2 and an acceptable carrier.

10. A composition comprising an insecticidally effective amount of the compound of claim 3 and an acceptable carrier.

11. A composition comprising an insecticidally effective amount of the compound of claim 5 and an acceptable carrier.

12. A composition comprising an insecticidally effective amount of the compound of claim 6 and an acceptable carrier.

13. A composition comprising an insecticidally effective amount of the compound of claim 7 and an acceptable carrier.

14. A composition for the inhibition of ecdysis in insects comprising the compound of claim 1.

15. A composition for the inhibition of ecdysis in insects comprising the compound of claim 2.

16. A composition for the inhibition of ecdysis in insects comprising the compound of claim 3.

17. A composition for the inhibition of ecdysis in insects comprising the compound of claim 5.

18. A composition for the inhibition of ecdysis in insects comprising the compound of claim 6.

19. A composition for the inhibition of ecdysis in insects comprising the compound of claim 7.

20. A process for the control of insects comprising the application of the composition of any of claims 1–19 to an area where it is desired to control said insects.

21. The process of claim 20 wherein said application is accomplished by spraying.

22. The process of claim 20 wherein said application is accomplished by distributing said compositions on or about the roots of growing plants.

23. An antifeedant comprising the compound of any of claims 1–7.

24. The antifeedant of claim 23 wherein said composition is a systemic.

25. A process for controlling insects comprising the application of the compound of claim 1 to an area where it is desired to control said insects in an amount of at least about 5 grams per acre.

26. The process of claim 25 wherein said compound is applied in an amount of about 50 grams per acre.

* * * * *

UNITED STATES PATENT AND TRADEMARK OFFICE
CERTIFICATE OF CORRECTION

PATENT NO. : 5,047,242

DATED : September 10, 1991

INVENTOR(S) : Klocke, Lee and Yamasaki

It is certified that error appears in the above-identified patent and that said Letters Patent is hereby corrected as shown below:

In the Abstract

At the first page, second column, line 4, please rewrite "tetrahydorazadirachtin" as --tetrahydroazadirachtin--.

At column 3, line 64, please rewrite "rroduct" as --product--. At column 4, line 64, please rewrite "palladiumon" as --palladium on--. At column 9, line 3, please rewrite "octadeylsilyl" as --octadecylsilyl--. At column 9, line 22, please replace "in press" with --10(6):1151-1163--.

UNITED STATES PATENT AND TRADEMARK OFFICE
CERTIFICATE OF CORRECTION

PATENT NO. : 5,047,242

DATED : September 10, 1991

INVENTOR(S) : Klocke, Lee and Yamasaki

It is certified that error appears in the above-identified patent and that said Letters Patent is hereby corrected as shown below:

In the Claims

At claim 1, please replace the incorrect formula with the formula of Fig. 2a. At claim 1, first line after the formula (beginning with "wherein") please rewrite "$R_3$" (first occurrence) as --$R_2$--.

FIG. 2a.

| | $R_1$ | $R_2$ | $R_3$ |
|---|---|---|---|
| 10 | H | H | Cinn |
| 12 | Ac | H | Cinn |
| 13 | Ac | Ac | Cinn |
| 14 | H | H | H |

Signed and Sealed this

Tenth Day of November, 1992

Attest:

DOUGLAS B. COMER

Attesting Officer

Acting Commissioner of Patents and Trademarks